(12) United States Patent
Neal

(10) Patent No.: US 6,414,027 B1
(45) Date of Patent: Jul. 2, 2002

(54) METHODS AND COMPOSITIONS FOR TREATING MALE ERECTILE DYSFUNCTION

(75) Inventor: Gary W. Neal, Knoxville, TN (US)

(73) Assignee: Androsolutions, Inc., Knoxville, TN (US)

( * ) Notice: Subject to any disclaimer, the term of this patent is extended or adjusted under 35 U.S.C. 154(b) by 0 days.

(21) Appl. No.: 09/215,295

(22) Filed: Dec. 18, 1998

Related U.S. Application Data (63) Continuation-in-part of application No. 08/890,445, filed on Jul. 9, 1997, now Pat. No. 6,103,765.
(60) Provisional application No. 60/068,294, filed on Dec. 19, 1997.

(51) Int. Cl.$^7$ .................... A61K 31/19; A61K 31/557

(52) U.S. Cl. .................................................. 514/573

(58) Field of Search .................... 514/167, 573

(56) References Cited

U.S. PATENT DOCUMENTS

| | | |
|---|---|---|
| 3,070,623 A | 12/1962 | Gottfried et al. |
| 3,161,654 A | 12/1964 | Shen |
| 3,647,858 A | 3/1972 | Hinkley et al. |
| 3,654,349 A | 4/1972 | Shen et al. |
| 3,657,327 A | 4/1972 | Morozowich |
| 3,781,429 A | 12/1973 | Partridge et al. |
| 3,800,038 A | 3/1974 | Rudel |
| 3,843,681 A | 10/1974 | Demerson et al. |
| 3,911,124 A | 10/1975 | Robert |
| 3,927,213 A | 12/1975 | Lippmann |
| 3,928,588 A | 12/1975 | Robert |
| 3,948,254 A | 4/1976 | Zaffaroni |
| 3,965,143 A | 6/1976 | Collins et al. |
| 3,967,618 A | 7/1976 | Zaffaroni |
| 3,976,660 A | 8/1976 | Ondetti et al. |
| 4,014,987 A | 3/1977 | Heller et al. |
| 4,038,415 A | 7/1977 | Rajadhyaksha et al. |
| 4,060,691 A | 11/1977 | Collins et al. |
| 4,085,135 A | 4/1978 | Kyogoku et al. |
| 4,112,942 A | 9/1978 | Scaife |
| 4,127,118 A | 11/1978 | Latorre |
| 4,128,577 A | 12/1978 | Nelson |
| 4,178,457 A | 12/1979 | Van Horn et al. |
| 4,198,406 A | 4/1980 | Hardy et al. |
| 4,215,128 A | 7/1980 | Howarth |
| 4,254,145 A | 3/1981 | Birnbaum |
| 4,271,314 A | 6/1981 | Collins et al. |
| 4,311,707 A | 1/1982 | Birnbaum et al. |
| 4,352,790 A | 10/1982 | Johansson et al. |
| 4,454,339 A | 6/1984 | Skuballa et al. |
| 4,503,040 A | 3/1985 | Barth |
| 4,507,323 A | 3/1985 | Stern |
| 4,521,421 A | 6/1985 | Foreman |
| 4,539,333 A | 9/1985 | Moncada |
| 4,564,362 A | 1/1986 | Burnhill |
| 4,680,312 A | 7/1987 | Johnson |
| 4,683,328 A | 7/1987 | Collins et al. |
| 4,684,633 A | 8/1987 | Imagawa et al. |
| 4,725,439 A | 2/1988 | Campbell et al. |
| 4,766,889 A | 8/1988 | Trick et al. |
| 4,801,587 A | 1/1989 | Voss et al. |
| 4,818,517 A | 4/1989 | Kwee et al. |
| 4,829,991 A | 5/1989 | Boeck |
| 4,857,059 A | 8/1989 | Rey et al. |
| 4,867,982 A | 9/1989 | Campbell et al. |
| 4,961,931 A | 10/1990 | Wong |
| 4,976,692 A | 12/1990 | Atad |
| 5,015,431 A | 5/1991 | Charkoudian |
| 5,049,384 A | 9/1991 | Kim |
| 5,059,603 A | 10/1991 | Rubin |
| 5,145,852 A | 9/1992 | Virag |
| 5,147,855 A | 9/1992 | Gozes et al. |
| 5,190,967 A | 3/1993 | Riley |
| 5,242,391 A | 9/1993 | Place et al. |
| 5,256,652 A | 10/1993 | El-Rashidy |
| 5,270,323 A | 12/1993 | Milne, Jr. et al. |
| 5,474,535 A | 12/1995 | Place et al. |
| 5,482,039 A | 1/1996 | Place |
| 5,565,466 A | 10/1996 | Gioco et al. |
| 5,571,118 A | 11/1996 | Boutos |
| 5,574,068 A | 11/1996 | Stamler et al. |
| 5,576,290 A | 11/1996 | Hadley |
| 5,583,144 A | 12/1996 | Kral |
| 5,601,343 A | 2/1997 | Hoffken |
| 5,612,314 A | 3/1997 | Stamler et al. |
| 5,631,284 A | 5/1997 | Legzdins et al. |
| 5,646,181 A | 7/1997 | Fung et al. |
| 5,648,393 A | 7/1997 | Stamler et al. |

(List continued on next page.)

FOREIGN PATENT DOCUMENTS

| | | |
|---|---|---|
| EP | 0 357 581 | 3/1990 |
| WO | WO 94/28902 | 12/1994 |
| WO | WO 96/16644 | 6/1996 |
| WO | WO 99/21558 | 5/1999 |

OTHER PUBLICATIONS

Robert J. Krane et al., N. Eng. J. Med, vol. 321, No. 24, pp. 1648–1659, 1989.
Virag, et al., Angiology, vol. 35, pp. 79–87, 1984.
N. Ishii et al., J. of Urol., vol. 141, pp. 323–325, 1989.
Schmidt, Jama, vol. 259, No. 21, p. 3176, 1988.

(List continued on next page.)

Primary Examiner—Theodore J. Criares
(74) Attorney, Agent, or Firm—Zoltick Technology Law Group, PLLC (57) ABSTRACT

Administration of a pharmaceutical composition in the form of a suppository comprising:
(a) a prostaglandin vasodilator;
(b) 15-hydroxyprostaglandindehydrogenase inhibitor; and
(c) a base material that is solid at room temperature and releases components (a) and (b) when inserted in the urethra,
is effective for the treatment of male erectile dysfunction.

26 Claims, 3 Drawing Sheets

U.S. PATENT DOCUMENTS

| | | | |
|---|---|---|---|
| 5,681,850 | A | 10/1997 | Frolich et al. |
| 5,698,225 | A | 12/1997 | Gimet et al. |
| 5,698,589 | A | 12/1997 | Allen |
| 5,708,031 | A | 1/1998 | Scott |
| 5,718,917 | A | 2/1998 | See |
| 5,731,339 | A | 3/1998 | Lowrey |
| 5,741,523 | A | 4/1998 | Teagarden et al. |
| 5,769,088 | A | 6/1998 | Place |
| 5,770,230 | A | 6/1998 | Teagarden et al. |
| 5,770,606 | A | 6/1998 | El-Rashidy et al. |
| 5,773,020 | A | 6/1998 | Place et al. |
| 5,820,587 | A | 10/1998 | Place |
| 5,855,548 | A | 1/1999 | Place |
| 5,877,216 | A | 3/1999 | Place et al. |
| 5,886,039 | A | 3/1999 | Kock et al. |
| 5,891,915 | A | 4/1999 | Wysor et al. |
| 5,905,091 | A | 5/1999 | Fuller |
| 5,919,474 | A | 7/1999 | Place et al. |
| 5,922,341 | A | 7/1999 | Smith et al. |
| 5,925,629 | A | 7/1999 | Place |

OTHER PUBLICATIONS

Bergstrom et al., J. Biol. Chem., vol. 238, pp. 3555–3564, 1963.
Corey et al., J. Am. Chem. Soc., vol. 91, p. 535, 1969.
Corey et al., J. Am. Chem. Soc., vol. 92, p. 2586, 1970.
Sih et al., J. Am. Chem. Soc., vol. 94, p. 3643, 1972.
Sih et al., J. Am. Chem. Soc., vol. 95, p. 1676, 1973.
Schaaf et al., J. Org. Chem., vol. 37, p. 2921, 1974.
Slates et al., Tetrahedron, vol. 30, pp. 819–830, 1974.
Corey et al., J. Am. Chem. Soc., vol. 92, p. 397, 1970.
Heather et al., Tetradedron Letters, pp. 2313–2316, 1973.
Mak et al., Biochimica et Biophysica Acta, vol. 1035, pp. 190–196, 1990.
Ensor et al., J. Lipid Mediators Cell Signalling, vol. 12, pp. 313–319, 1995.
Chang et al., Biochem, Biophys, Res. Commun., vol. 99, pp. 745–751, 1981.
Jarabak et al., Prostaglandins, vol. 18, pp. 241–246, 1979.
Lin et al., Biochem, Biophys, Res. Commun., vol. 81, pp. 1227–1234, 1978.
Hosoda et al., J. Org. Chem., vol. 38, p. 4209, 1973.
Herin Padam–Nathan et al., New England Journal of Medicince, vol. 336, pp. 1–7, Jan. 2, 1997.
Rosen et al., Archives of Sexual Behavior, vol. 22(6), pp. 521–543, 1993.
G.M. Craig, PMJ, vol. 51, pp. 74–84, 1975.
J. Lopiccolo et al., J. of Counseling and Clinical Psychology, vol. 54(2), pp. 158–167, 1986.
Gringanz, Introduction to Medicinal Chemistry, Wiley–VCH, Inc. New York, pp. 155–161 and 640–643, 1997.
Yamamura et al., J. Chromatogr., vol. 331, pp. 383–388, 1985.
Uekama et al., J. Pharm. Sci., vol. 73, pp. 382–384, 1984.
Yamamura et al., J. Chromatorgr., vol. 303, pp. 165–172, 1984.
Merck Index, 10$^{th}$ Edition, citation 4368, 1983.
Berry et al., Biochemical Pharmacology, vol. 32, pp. 2863–2871, 1983.
H. Willimann et al., J. of Pharmaceutical Sciences, vol. 81, pp. 871–874, 1992.
Goldstein et al, Abstract #919, The Journal of Urology, V. 159(5), p. 240, May 1998.
M. Muramatsu, Biochemical Pharmacology, vol. 33, pp. 2629–2633, 1984.
C.L. Tai et al., Biochem. J., vol. 267, pp. 75–78, 1990.
H. Hedlund et al., J. Urol., vol. 134, pp. 1245–1250, 1985.
F. Pichaud et al., Blood, vol. 89, pp. 2105–2112, 1997.
M. Waldhauser et al., J. Urology, vol. 140, pp. 525–527, 1988.
M.E. Baker, Steroids, vol. 59, pp. 136–141, 1994.
H. Porst, J. Urology, vol. 155, pp. 802–815, 1996.
K. Takeuchi et al, Gen. Pharmac., vol. 30, pp. 739–744, 1988.
A.C. Roy et al., Brit J. Urology, vol. 64, pp. 180–182, 1989.
E. Anggard et al., Agents and Actions, vol. 6/4, pp. 498–504, 1976.
G. Galea et al., J. Urology, vol. 159, p. 236, Abstract No. 903, 1998.
S. Sakuma et al., Prostaglandins, vol. 40, pp. 507–514, 1990.
J. Jarabak, Prostaglandins, vol. 35, pp. 403–411, 1988.
Y. Iljima et al., Biochem, and Biophys, Res. Comm., vol. 80, pp. 484–489, 1978.
D.T.Y. Kung–Chao et al., Biochemica et Biophysica Acta, vol. 614, pp. 1–13, 1980.
C.G. Stief et al., J. Urology, vol. 159, pp. 1390–1393, 1998.
Peskar et al., J. Pharm. Pharmacol., vol. 28, pp. 146–148, 1976.
Virag et al., J. Urology, vol. 137, p. 1010, 1987.
Linet et al., New England Journal of Medicine, vol. 334, pp. 873–877, Apr. 4, 1996.
Wolfson et al., Urology, vol. 42, pp. 73–75, 1993.
Diagnostic and Statistical Manual IV, "Sexual and Gender Identity Disorder", American Psychiatric Association, Washington, D.C., pp. 493–539 and 735–751, 1994.
Nathan, J. of Sex and Marital Therapy, vol. 12, No. 4, pp. 267–281, 1986.
Osborn et al., British Medical Journal, vol. 296, pp. 959–962, 1988.
Frank et al., New England Journal of Medicine, vol. 299, pp. 111–115, 1978.
Basar et al., International Urology and Nephrology, vol. 29, pp. 667–671, 1997.
Proceeding of the American Urological Association, vol. 153, Apr. 1995 Supplement, Abstracts 976 and 977.
Änggård et al., Ark . Kem., vol. 25, pp. 293–300, 1996.
Garde et al., Maturitas, vol. 2, pp. 225–240, 1980.
Handelsman, "Diagnosis and Treatment of Impotence" in AHCPR Health Technolgy Assessment Reports, No. 2, pp. 1–24, 1990.
Bergstrom et al., Acta Chem. Scand., vol. 16, p. 501–504, 1962.
MacDonald, Biochem, Biophys, Acta., vol. 1061, pp. 297–303, 1991.
Althof et al., J. Sex & Marital Therapy, vol. 13, pp. 155–167, 1987.
Benkert et al., Psychopharmacologia, vol. 23, pp. 91–95, 1972.
Utiger, N. England J. Med., vol. 338, pp. 1458–1459, 1998.
Siegel–Itzkovich, BMJ, vol. 316, p. 1625, 1998.
Bodner et al., J. Urol., vol. 138, pp. 310–3111, 1987.
Lal et al. Prog. Neuro–Pschopharmacol. & Biol. Psychiat., vol. 11, pp. 235–242, 1987.
Goldstein et al., N. England J. Med., vol. 338, pp. 1397–1404, 1998.

Hyyppä et al., in Sexual Behavior Pharmacology and Biochemistry, M. Sandler et al., Plenum Press, New York, pp. 315–327, 1975.
Virag et al., Angiol., vol. 35, pp. 79–87, 1984.
Virag et al., J. of Urol., vol. 137, p. 1010, 1987.
Chang, Advances in Prostaglandin, Thromboxane, and Leukotriene Research, vol. 19, pp. 225–228, 1989.
Cawello et al., Journal of Urology, vol. 158, pp. 1403–1407, 1997.
Van Ahlen et al., Journal of Urology, vol. 151, pp. 1227–1230, 1994.
Chen et al., Journal of Clinical Ultrasound, vol. 20, pp. 247–253, 1992.
Harrison's Principles of Internal Medicine, Thirteenth Ed., K.J. Isselbacher et al., Eds., McGraw–Hill, Inc., New York P. 2492, 1994.
Foldvari et al., European Journal of Drug Metalbolism and Pharmacokinetics, vol. 22(2), pp. 111–120, 1997.
Alam et al., Endocrinology, vol. 98 (4), pp. 859–863, 1976.
Franchi et al., Prostaglandins, vol. 29 (6), pp. 953–960, 1985.
Stackl et al., Journal of Urology, vol. 140, pp. 66–68, 1988.
Migeon et al., The Johns Hopkins Medical Journal, vol. 123, pp. 128–133, 1968.
Futterweit et al., Metabolism, vol. 33 (10), pp. 936–942, 1984.
Notification of Transmittal of the International Search Report of the Declaration issued on Nov. 17, 1998, in corresponding PCT/US98/13439.
Written Opinion issued on Jul. 12, 1999, in corresponding PCT Application No. PCT/US98/13439.
Goodman & Gilman et al., "The Pharmacological Basis of Therapeutics" ($6^{th}$ Edition), New York, pp. 668–678, 1980.
Robert C. MacDonald, Et al., "Small–Volume Extrusion Apparatus for Preparation of Large, Unilamellar Vesicles", pp. 297–303, Jul. 23, 1990.
Roy J. Levin, "The Physiology of Sexual Function in Women", pp. 213–253, vol. 7, No. 2, Aug. 1980.
Philip M. Sarrel, MD., "Sexuality and Menopause", pp. 26S–30S, Sep. 29, 1989.
Emre Akkus et al., "Duplex Ultrasonography After Prostaglandin E1 Injection of the Clitoris in a Case of Hyperreactio Luteinalis", pp. 1237–1238, vol. 153, Apr. 1995.
Prostaglandin 15–Hydroxydehydrogenase Activity in Human Penile Corpora Cavernosa and its Significance in Prostaglandin–Mediated Penile Erection, A.C. Roy, et al., *British Journal of Urology* (1989), 64, 180–182.
Endogenous Inhibitors of Human Placental Prostaglandin Dehydrogenase, M. Mibe, et al., *Prostaglandins Leukotrienes and Essential Fatty Acids* (1992) 46, 241–254.
Effect of 2'–Carboxymethoxy–4, 4'–Bis(3–Methyl–2–Butenyloxy)Chalcone (SU–88) on Prostaglandin Metabolism in Hog Gastric Mucosa, Makoto Muramatsu, et al., *Biochemical Pharmacology*, vol. 33, No. 16, (1984) 2629–233.
U.S. Serial No. 09/215,295 filing date Dec. 18, 1998, Pending.
U.S. Seral No. 09/391,412, filing date Sep. 8, 1999, Pending.

METHODS AND COMPOSITIONS FOR TREATING MALE ERECTILE DYSFUNCTION

This is a continuation-in-part of U.S. patent application Ser. No. 08/890,445, filed on Jul. 9, 1997, now U.S. Pat. No. 6,103,765, which is incorporated herein by reference in its entirety which claims the benefit of Provisional Application Ser. No. 60/068,294 filed Dec. 19, 1997.

BACKGROUND OF THE INVENTION

1. Field of the Invention

The present invention relates to methods of treating male erectile dysfunction. The present invention further relates to pharmaceutical compositions useful for treating male erectile dysfunction.

2. Discussion of the Background

Impotence, or lack of a man's ability to have sexual intercourse, is often the subject of jokes. However, millions of men suffer from this condition. Impotence is generally characterized by an inability to maintain a penile erection, and is often referred to as erectile dysfunction. Erectile dysfunction affects men, regardless of age, place of birth, or prior sexual experience.

In the context of the present invention, the term "erectile dysfunction" refers to certain disorders of the cavernous tissue of the penis and the associated fascia which produce impotence, the inability to attain a sexually functional erection. Impotence is estimated to affect about 10 million men in the United States alone. Impotence results from disruption of any of numerous physiological or psychological factors which cause the blood flow to and from the penis to remain in balance thereby preventing retention of sufficient blood to cause rigid dilation of the corpus cavernosa and spongiosa. In the context of the present invention, the term "impotence" is used in its broadest sense as the inability to attain a sexually functional erection when desired.

Treatments for impotence include psychosexual therapy, hormonal therapy, administration of vasodilators such as nitroglycerin and α-adrenergic blocking agents (hereafter "α-blockers"), vascular surgery, implanted penile prostheses, vacuum devices and external aids such as penile splints to support the penis or penile constricting rings to alter the flow of blood through the penis, (see Robert J. Krause, et al., *N. Eng, J. Med.*, vol. 321, No 24, Dec. 14, 1989). Many patients treat their impotence by self injection of vasoactive drugs directly into the corpora cavernosa (see: Forward 1$^{st}$ *Symposium International Sur L'Erection Pharmacologique*, Nov. 17–19 1989, Paris, p. 2; Virag, et al., *Angiology*, vol. 35, pp. 79–87, (1984); and U.S. Pat. Nos. 4,127,118, 4,766,889, and 4,857,059, which are incorporated herein by reference). The drugs most commonly used include α-blockers, such as phenoxybenzamine and phentolamine; smooth muscle relaxants such as papaverine; prostaglandins having a vasoactive function such as prostaglandin $E_1$ and combinations of such drugs having different receptor effects to enhance therapy. Intracavernous injection doses of papaverine are typically in the range of about 7.5 to 160 mg, while doses of phentolamine are in the range of about 0.1 to 10 mg and doses of prostaglandin $E_1$ are in the range of about 2.5 to 50 micrograms (see for example. Kurkle, et al., *Urol. Clin. of America*, vol. 15, No. 4, pp. 625–629 (1988) and N. Ishii et al., *J. of Urol.*, vol. 141, pp. 323–325 (1989). Vasoactive intestinal peptides have also been reported as producing erection upon intracavernous injection at doses of 10–100 µg (see H. Handelsman. *Diagnosis and Treatment of Impotence*, U.S. Dept. of Health Services, Agency for Health Care Policy and Research, April 1990).

However, patients often find the injections of vasoactive drugs psychologically disturbing, painful, traumatic, or inconvenient as evidenced by a high discontinuance rate (see S. Althouf, et al., *Journal of Sex and Marital Therapy*, vol. 15, No. 2, pp. 121–129 (1989). In addition, adverse side effects including priapism, corporeal nodules and diffuse fibrosis, drug tolerance, bruising and hematomas, swelling and ulceration of the penile skin at the injection site have also been reported.

U.S. Pat. No. 4,801,587 and EPA 0357581 disclose the administration of vasodilators via the male urethra to produce erections. The transurethral administration of testosterone has also been reported (see S. M. Milco, *Bulletins et Memoirs de la Societa Roumaine D'Endocrinologie*, Vol. 5, pp. 434–437 (1989)). It has also been suggested that cocaine administered transurethrally could contribute to an erection (*JAMA*, vol. 259, No. 21. page 3176 (1988)). A nitroglycerin coated, erection inducing condom is disclosed in U.S. Pat. No. 4,829,991.

However, to date there is no completely effective treatment for male erectile dysfunction. Thus, there remains a need for a method of treating male erectile dysfunction. There also remains a need for compositions which are effective for treating male erectile dysfunction. In particular, there remains a need for methods and compositions for treating impotence which are characterized by a reduced tendency to cause pain, priapism, corporeal nodules, diffuse fibrosis, and scarring.

SUMMARY OF THE INVENTION

Accordingly, it is one object of the present invention to provide novel methods for treating male erectile dysfunction.

It is another object of the present invention to provide methods for treating male erectile dysfunction involving topical, mental, and/or transurethral administration of a pharmaceutical composition.

It is another object of the present invention to provide methods for treating male erectile dysfunction which exhibit a reduced tendency to cause pain or a burning sensation.

It is another object of the present invention to provide methods for treating male erectile dysfunction which exhibit a reduced tendency to cause priapism.

It is another object of the present invention to provide methods for treating male erectile dysfunction which exhibit a reduced tendency to cause corporeal nodules.

It is another object of the present invention to provide methods for treating male erectile dysfunction which exhibit a reduced tendency to cause diffuse fibrosis.

It is another object of the present invention to provide methods for treating male erectile dysfunction which exhibit a reduced tendency to cause scarring of the corpora spongiosum and cavernosa.

It is another object of the present invention to provide novel pharmaceutical compositions which are useful for treating male erectile dysfunction.

It is another object of the present invention to provide pharmaceutical compositions for treating male erectile dysfunction which exhibit a reduced tendency to cause pain or a burning sensation.

It is another object of the present invention to provide pharmaceutical compositions for treating male erectile dysfunction which exhibit a reduced tendency to cause priapism.

It is another object of the present invention to provide pharmaceutical compositions for treating male erectile dysfunction which exhibit a reduced tendency to cause corporeal nodules.

It is another object of the present invention to provide pharmaceutical compositions for treating male erectile dysfunction which are effective when applied topically, meatally, and/or transurethrally.

It is another object of the present invention to provide pharmaceutical compositions for treating male erectile dysfunction which exhibit a reduced tendency to cause diffuse fibrosis.

It is another object of the present invention to provide pharmaceutical compositions for treating male erectile dysfunction which exhibit a reduced tendency to cause scarring of the corpora spongiosum and cavernosa.

These and other objects, which will become clear in the course of the following detailed description, have been achieved by the inventor's discovery that pharmaceutical compositions, which are in the form of a urethral suppository, and which comprise:

(a) a prostaglandin vasodilator;
(b) a 15-hydroxyprostaglandindehydrogenase inhibitor; and
(c) a base material that is solid at room temperature and releases components (a) and (b) when inserted in the urethra, are particularly effective for the treatment of male erectile dysfunction even at low doses.

In a preferred embodiment, component (c) is a base material that is solid at room temperature but melts or dissolves when inserted in the urethra to release components (a) and (b).

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DETAILED DESCRIPTION OF THE PREFERRED EMBODIMENTS

Thus, in a first embodiment, the present invention provides novel pharmaceutical compositions which are useful for treating male erectile dysfunction. The present pharmaceutical compositions are characterized as being in the form of a urethral suppository and comprising:

(a) a prostaglandin vasodilator;
(b) a 15-hydroxyprostaglandindehydrogenase inhibitor; and
(c) a base material that is solid at room temperature and releases components (a) and (b) when inserted in the urethra.

Examples of suitable prostaglandins include, but are not limited to, PGE-1; PGE-2; PGF-2α; PGA-1; PGB-1; PGD-2; PGE-M; PGF-M; PGH-2; PGI-2; 19-hydroxy-PGA-1; 19-hydroxy-PGB-1; PGA-2; PGB-2; 19-hydroxy-PGA-2; 19-hydroxy-PGB-2; PGB-3; PGF-1α; 15-methyl-PGF-2α; 16,16-dimethyl-$\Delta^2$-PGE-1 methyl ester; 15-deoxy-16-hydroxy-16-methyl-PGE-1 methyl ester; 16,16-dimethyl-PGE-2; 11-deoxy-15-methyl-PGE-1; 16-methyl-18,18,19,19-tetrahydrocarbacyclin; (16RS)-15-deoxy-16-hydroxy-16-methyl-PGE-1 methyl ester; (+)-4,5-didehydro-16-phenoxy-α-tetranor-PGE-2 methyl ester; 11-deoxy-11a,16,16-trimethyl-PGE-2; (+)-11a,16a,b-dihydroxy-1,9-dioxo-1-(hydroxymethyl)-16-methyl-trans-prostene; 9-chloro-16,16-dimethyl-PGE-2; arboprostil; iloprost; CL 115,347, and semisynthetic or synthetic derivatives of these natural prostaglandins, or any derivative or any prostaglandin analog capable of acting as a vasodilator or neuromodulator. Cyclodextrin complexes are also included as they may enhance the activity of the solution and stabilize the prostaglandin. Racemic, optically enriched or purified stereoisomers of any of these compounds are also included. Physiologically acceptable salts are also included. Preferably, the prostaglandin is PGE-1, PGE-2, PGF-2α, PGD-2, PGF-1α, 15-methyl-PGF-2α, and CL 115,347. Most preferably, the prostaglandin is PGE-2 or PGE-1.

PGE-1, prostaglandin $E_1$ is also known as alprostadil or $PGE_1$. The formal chemical name of PGE-1 is 3-hydroxy-2-(3-hydroxy-1-octenyl)-5-oxocyclopentaneheptanoic acid, and the structure of PGE-1 is Prostaglandin $E_1$ may be isolated from sheep seminal vesicle tissue as described in Bergstrom et al., *Acta. Chem. Scand.*, vol. 16, p. 501 (1962) and *J. Biol. Chem.*, vol. 238, p. 3555 (1963). The synthesis of prostaglandin $E_1$ may be carried out as described in Corey et al., *J. Am. Chem. Soc.*, vol. 91, p. 535 (1969); Corey et al., *J. Am. Chem. Soc.*, vol. 92, p. 2586 (1970); Sih et al. *J. Am. Chem. Soc.*, vol. 94, p. 3643 (1972); Sih et al., *J. Am. Chem. Soc.*, vol. 95, p. 1676 (1973); Schaaf et al., *J. Org. Chem.*, vol. 37, p. 2921 (1974); and Slates et al., *Tetrahedron*, vol. 30, p. 819 (1974).

PGE-2, prostaglandin $E_2$ is also known as dinoprostone or $PGE_2$. The formal chemical name of PGE-2 is 7-[3-hydroxy-2-(3-hydroxy-1-octenyl)-5-oxocyclopentyl]-5-heptenoic acid, and the structure of PGE-2 is:

Prostaglandin $E_2$ may be isolated from sheep seminal vesicle tissue as described in Bergstrom et al., *Acta. Chem. Scand.*, vol. 16, p. 501 (1962). Prostaglandin $E_2$ may be synthesized as described in Corey et al., *J. Am. Chem. Soc.*, vol 92, p. 397 (1970); Corey et al., *J. Am. Chem. Soc.*, vol. 92, p. 2586 (1970); and Heather et al., *Tetrahedron Letters*, p. 2313 (1973).

Both prostaglandin $E_1$ and $E_2$ are commercially available from Sigma Chemical Company of St. Louis, Mo. PGE-2 is also commercially available as a Prostin E-2 suppository and as Prepidil Gel from Pharmacia & UpJohn Company, Kalamazoo, Mich., and as Cervidil from Forrest Pharmaceuticals, Inc., St. Louis, Mo.

PGF-2α, prostaglandin $F_{2\alpha}$, is also known as dinoprost or $PGF_{2\alpha}$. The formal chemical name is 7-[3,5-dihydroxy-2-(3-hydroxy-1-octenyl)cyclopentyl]-5-heptenoic acid. PGF-2α may be prepared as described in U.S. Pat. No. 3,657,327, which is incorporated herein by reference.

15-Deoxy-16-hydroxy-16-methyl-PGE-1 methyl ester is also known as misoprostol and has the formal chemical name of (±)-methyl-(1R,2R,3R)-3-hydroxy-2-[(E)-(4RS)-4-hydroxy-4-methyl-1-octenyl]-5-oxocyclopentaneheptanoate. 15-Deoxy- 16-hydroxy-16-methyl-PGE-1 methyl ester may be prepared as described in U.S. Pat. No. 3,965,143, which is incorporated herein by reference.

Enprostil has the formal chemical name of [1α,2β(1E,3R*),3α]-7-[3-hydroxy-2-(3-hydroxy-4-phenoxy-1-butenyl)-5-oxocyclopentyl]-4,5-heptadienoic acid methyl ester. Enprostil may be prepared as described in U.S. Pat. No. 4,178,457, which is incorporated herein by reference.

PGI-2is also known as prostacyclin, epoprostenol, prostaglandin $I_2$, prostaglandin X, $PGI_2$, and PGX. Prostacyclin may be prepared as described in U.S. Pat. No. 4,539,333, which is incorporated herein by reference.

The remaining prostaglandins are described in Alex Gringanz, *Introduction to Medicinal Chemistry*, Wiley-VCH, Inc., New York, pp. 158–159 and 641–642, 1997, which is incorporated herein by reference.

Cyclodextrin complexes of the prostaglandin may be used in order to increase the stability and efficacy. Cyclodextrin complexes may be prepared by adding the proper stoichiometric ratio of the prostaglandin to α, β, or γ cyclodextrin in an aqueous solvent and then either using as is or lyophilizing to provide a solid clathrate for mixing. These complexes are described in Yamamura et al. *J. Chromatogr.*, vol. 331, pp.383–388 (1985); Hirayama et al, *Chem. Pharm. Bull.*, vol. 32 pp. 4237–4240 (1984); Uekama et al,*J. Pharm. Sci.*, vol. 73, pp. 382–384 (1984); and Yamamura et al, *J. Chromatogr.*, vol. 303, pp. 165–172 (1984), which are incorporated herein by reference.

Typically, the present composition will contain prostaglandin $E_1$ or prostaglandin $E_2$ in an amount of 0.1 μg to 10 mg, preferably 10 to 1000 μg (for transurethral administration), preferably 25 to 2500 μg (for meatal administration), per unit dosage.

By the term "15-hydroxyprostaglandindehydrogenase inhibitor" it is meant any compound which exhibits a significant and selective inhibition of prostaglandin degrading enzyme, or 15-hydroxyprostaglandindehydrogenase (PGDH). Two forms of 15-hydroxyprostaglandindehydrogenase (PGDH) are known: Type I, which is $NAD^+$ dependent, and Type II, which is $NADP^+$ dependent. Type I operates at a Km one order of magnitude lower than Type II and is thus more significant physiologically. Type I PGDH is described in Mak et al. *Biochimica et Biophysica Acta*, vol. 1035, pp. 190–196 (1990); Ensor et al, *J. Lipid Mediators Cell Signalling*, vol. 12. pp. 313–319 (1995); and Berry et al, *Biochemical Pharmacology.* vol. 32, no. 19, pp. 2863–2871 (1983), which are incorporated herein by reference. Partially purified bovine lung Type I PGDH is commercially available from BDH, Limited (Poole, UK). Berry et al., Tai et al., Muramatsu et al., and Mak et al. describe assays for determining enzymatic activity of Type I PGDH as well as methods for determining the degree of inhibition of this enzyme.

Type II PGDH is described in Chang, et al, *Biochem. Biophys. Res. Commun.*, vol. 99. pp. 745–751 (1981); Jarabak, et al. *Prostaglandins, vol.* 18, pp. 241–246 (1979). and Lin. et al, *Biochem. Biophys. Res. Commun.*, vol. 81, pp. 1227–1234 (1978), all of which are incorporated herein by reference.

Examples of suitable 15-hydroxyprostaglandindehydrogenase inhibitors include but are not limited to glycyrrhizic acid, licorice, glycyrrhetinic acid, various glycosides of glycrrhetinic acid, carboxenolone, DHEA, spironolactone, sofalcone, indomethacin, sulindac, etodolac, oleic acid, palmitic acid, and sulphasalazine and analogues thereof. Antibodies which bind to and inhibit Type I PGDH may also be used.

Glycyrrhizic acid is also known as glycyrrhizin, glycyrrhizinic acid, and glycyrrhetinic acid glycoside. The formal chemical name is 20β-carboxy-11-oxo-30-norolean-12-en-3β-yl-2-O-β-D-glucopyranuronosyl-α-D-glucopyranosiduronic acid, and the structure is:

Glycyrrhizic acid is commercially available from Sigma Chemical Company of St. Louis, Mo.

Glycyrrhetinic acid is unglycosylated glycyrrhizic acid, and its structure is:

Glycyrrhetinic acid may be obtained from licorice extract.

Carbenoxolone is also known as 3β-hydroxy-11-oxo-20β-olean-12-en-29-oic acid hydrogen butanedioate and has the following structure:

Carbenoxolone may be synthesized as described in U.S. Pat. No. 3,070,623, which is incorporated herein by reference.

Licorice is also known as sweet root liquorice and glycyrrhiza and is described in the Merck Index, 10th edition, citation 4368 as "glycyrrhiza, Licorice, liquorice; sweet root. Dried rhizome and root of Glycyrrhiza glabra L., var. typica Regel & Herder (Spanish licorice), or of G. Glabra L., var. glandulifera (Waldst. & Kit.) Regel & Herder (Russian licorice), or of other varieties of G. g yielding a yellow and sweet wood, Leguminosaw. Habt. Southern Europe to Central Asia. Constit. 6–14% glycyrrhizin (the glucoside of glycyrrhetic acid), asparagine, sugars, resin."

Licorice is a crude preparation prepared from dried rhizomes or roots and as such contains large numbers of compounds many of which are not identified. A simple aqueous extract of a commercially available dried licorice root preparation may be prepared as follows. Two grams of this dried licorice root was mixed with 10 mls of distilled water, stirred until thoroughly mixed at room temperature and filtered to remove particulate matter. This simple aqueous extract of licorice is effective in inhibiting PGDH and may be used as is in the present invention.

Spironolactone is also known as Aldactone A or Verospiron. The formal chemical name of spironolactone is 17-hydroxy-7-mercapto-3-oxo- 17α-pregn-4-ene-21-carboxylic and γ-lactone, 7-acetate, and the structure is:

Spironolactone is commercially available from Sigma Chemical Company of St. Louis, Mo.

Sofalcone is formally known as [5-[(3-methyl-2-butenyl)oxy]-2-[3-[4[(3-methyl-2-butenyl)oxy]phenyl]-1-oxo-2-propenyl]phenoxy]acetic acid and has the formula:

Sofalcone may be prepared as described in U.S. Pat. No. 4,085,135, which is incorporated herein by reference.

DHEA is formally known as 3-hydroxyandrost-5-en-17-one or dehydroepiandrosterone or prasterone. The structure of DHEA is:

DHEA may be prepared as described in H. Hosoda et al, *J. Org. Chem.*, vol. 38, p. 4209 (1973), which is incorporated herein by reference.

Sulfasalazine is also known as 2-hydroxy-5[[4-[(2-pyridinylamino)sulfonyl]phenyl]azo]benzoic acid and has the structure:

A number of sulfasalazine analogs have been shown to be inhibitors of PGDH by Berry et al, *Biochemical Pharmacology*, vol. 32, pp. 2863–2871 (1983). Examples of sulfasalazine analogs which may be used as the PGDH inhibitor in the present compositions include:

-continued

-continued

Etodolac is also known as 1,8-diethyl-1,3,4,9-tetrahydropyrano-[3,4-b]indole-1-acetic acid. Etodolac may be prepared as described U.S. Pat. No. 3,843,681, which is incorporated herein by reference.

Indomethacin is also known as 1-(4-chlorobenzoyl)-5-methoxy-2-methyl-1 H-indole-3-acetic acid. Indomethacin may be prepared as described in U.S. Pat. No. 3,161,654, which is incorporated herein by reference.

Sulindac is also known as 5-fluoro-2-methyl-1-[[4-(methylsulfinyl)phenyl]methylene]-1H-indene-3-acetic acid. Sulindac may be prepared as described in U.S. Pat. Nos. 3,654,349 and 3,647,858, which are incorporated herein by reference.

Other types of 15-hydroxyprostaglandindehydrogenase inhibitors include aliphatic and aromatic carboxylic acids. Suitable carboxylic acids particularly include any straight chain or branched, saturated, monounsaturated, or polyunsaturated aliphatic $C_8$–$C_{31}$ carboxylic acid. Particularly preferred for use as component (b) in the present suppositories are free fatty acids including, but not limited to palmitic acid, oleic acid, stearic acid, capric acid, lauric acid, myristic acid, linoleic acid, arachidic acid and arachadonic acid, all of which are commercially available from Sigma Chemical Co., St. Louis, Mo.

The 15-hydroxyprostaglandindehydrogenase inhibitor will typically be present in an amount of 25 to 100, preferably 50 to 100, pig penile units of PGDH inhibition activity, per unit dosage. The amount of inhibitor which corresponds to a unit of pig penile PGDH inhibition activity is determined using either the spectrophotometric or radio-chemical assay described in the Examples. For inhibitors which exhibit a significant absorption at 340 nm, it is preferred to use the radio-chemical assay.

When the 15-hydroxyprostaglandindehydrogenase inhibitor is a fatty acid, such as palmitic acid, oleic acid, stearic acid, capric acid, lauric acid, myristic acid, linoleic acid, arachidic acid and arachadonic acid, the fatty acid will suitably be present in the suppository in an amount of from about 0.1 µg to about 20 mg, preferably from about 100 µg to about 10 mg.

When the 15-hydroxyprostaglandindehydrogenase inhibitor is etodolac, sulindac, or indomethacin, the suppository will suitably contain the 15-hydroxyprostaglandindehydrogenase inhibitor in an amount of 0.1 Mg to 20 mg, preferably 0.5 mg to 10 mg, per unit dosage of prostaglandin.

Component (c), the base or carrier material, may be composed of any material or mixture of materials that is compatible with component (a), the prostaglandin vasodilator, and component (b), the 15-hydroxyprostaglandindehydrogenase inhibitor, and which releases components (a) and (b) upon insertion into the meatus or urethra. Examples of materials suitable for use as component (c) which releases components (a) and (b) upon insertion of the suppository into the urethra include materials such as hydrogels which contain or are saturated with components (a) and (b).

Examples of suitable gels include triacetin, hydroxycellulose, gels composed of water, propylene glycol, hydroxypropyl methylcellulose and any other gels which are compatible with the prostaglandin. A particularly preferred gel is lecithin organogel prepared according to H. Willimann et al. "Lecithin organolgel as matrix for transdermal transport of drugs," *J. Pharm. Sci.*, vol. 81 (9), pp. 871–874 (1992), which is incorporated herein by reference. This particular preparation exhibits a dramatically enhanced potency.

One may also use a gel in which one or more of the prostaglandins or co-agents is released in a controlled-released manner (i.e., released over time) to prolong the effect of the composition. For example, components (a) and (b) can be formulated into a cross-linked polyethylene oxide/urethane polymer which is well tolerated by living tissues and releases components (a) and (b) in a controlled release manner. Controlled release compositions are disclosed in D. H. Lewis, *Controlled Release of Pesticides and Pharmaceuticals*, Plenum Press, New York, 1981; and A. F. Kydonieus. *Controlled Release Technologies; Methods, Theory, and Applications*, CRC Press, Boca Raton, 1980, which are incorporated herein by reference.

In a preferred embodiment, component (c) is a material or mixture of materials which is compatible with component (a), the prostaglandin vasodilator, and component (b), the 15-hydroxyprostaglandindehydrogenase inhibitor, and which results in the final composition having a melting point ranging from about 70° to about 100° F. preferably from about 70° to about 90° F.

Specific examples of suitable materials for use as component (c) include but are not limited to fatty acid esters, such as ethyl stearate, methyl stearate, isopropyl stearate, butyl stearate, and cetyl lactate; fatty acid ethers, such as laureth 9; cholesterol esters such as cholesteryl oleate and cholesteryl palmitate; cholesterol ethers; fatty acid diglycerides; fatty acid triglycerides; fatty acids; phospholipids; glycolipids; and sphingolipids. Ethyl stearate is a particularly preferred compound for use as component (c).

Other materials suitable for use as component (c) include polyethylene glycol (PEG). The PEG is chosen so that the suppository is a solid or semisolid at room temperature but melts/dissolves rapidly in the urethra. Good results have been achieved using PEG with an average molecular weight of about 1450.

The present suppositories may further comprise one or more co-agents. Examples of suitable co-agents include:

1. ACE inhibitors, including but not limited to captopril, enalapril, enalaprilat, quinapril, lisinopril, and ramipril, may enhance the efficacy of the present method and decrease long term complications, such as inflammatory and fibrotic responses;
2. Nitro vasodilators, including but not limited to nitroglycerin, isosorbide dinitrate, amyl nitrate, isosorbide mononitrate, erythrityl tetranitrate, and sodium nitroprusside, may enhance the efficacy of the present method;
3. Alpha blockers, including but not limited to prazosin, phentolamine, phenoxybenzamine, dibenzamine, doxazosin, terazosin, trimazosin, tolazoline, corynthanine, rauwolscine, and piperoxan, are especially desirable for increasing the efficacy and prolonging the action of the present method.
4. Other adrenoreceptor agents, including but not limited to yohimbine, labetalol, carvedilol, and bucindolol, may also enhance the activity and prolong the action of the present method;
5. Phosphodiesterase (PDE) inhibitors, including but not limited to caffeine, aminophylline, theophylline, amrinone, milrinone, vesnarinone, vinpocetine, pemobendan, cilostamide, enoximone, peroximone, rolipram, R020–1724, zaniprast, dipyridamole, and sildenafil, may also be effective in enhancing the efficacy of the present method and for prolonging the effect;
6. Muscarinic agents such as pilocarpine, edrophonium, and bethanacol;
7. Dopaminergic agonists such as apomorphine and bromocriptine;
8. Ergot alkaloids such as ergotamine and ergotamine analogs, including acetergamine, bravergoline, bromerguride, clanegollone, ergonovine, ergotamine tartrate, and pergolide;
9. Opiate antagonists such as naloxone, naltrexone, nalmefene, nalorphine, methyl naltrexone, CTOP, diprenorphine, β-funaltrexamine, naloxonazine, norbinaltorphimine, natrindole, BNTX, and other analogs, which exhibit opioid antagonistic properties;
10. Polypeptide neurotransmitters such as VIP, calcitonin, calcitonin gene related product, VIP analogs, and cholecystokinin and all its analogs such as CCK8; and
11. Mast cell stabilizers such as chromolyn, nedochromolyn, zileuton, piripost, MK-886, MK-0591, ICI-D2318, docebenone, and leukotriene receptor antagonists.

Particularly desirable compositions include alpha-blockers and/or PDE inhibitors. Any combinations of the single above-listed compounds or multiple combinations of different compounds or different groups may also be used. In some instances, it may be advantageous to pretreat with one or more of the co-agents. For example, pretreatment with a PGDH inhibitor followed by treatment with PGE will enhance the efficacy of the present method.

The present urethral suppositories will typically be oblong in shape with a length to width aspect ratio of from about 1:1 to about 75:1, preferably from about 5:1 to about 20:1. The length of the suppository may vary from about 1 mm to about 100 mm. preferably from about 2 mm to about 75 mm. The length of the suppository may be tailored to direct the dosage of the prostaglandin to either the urethral meatus or the penile urethra. When administration to the urethral meatus is desired, the length of the suppository is preferably from about 2 mm to about 60 mm, more preferably from about 5 mm to about 50 mm, and most preferably from about 10 mm to about 40 mm. In contrast, when administration to the penile urethra is desired, the length of the suppository is preferably from about 50 mm to about 100 mm, more preferably from about 60 mm to about 100 mm, and most preferably from about 60 mm to about 80 mm.

Figure 2:
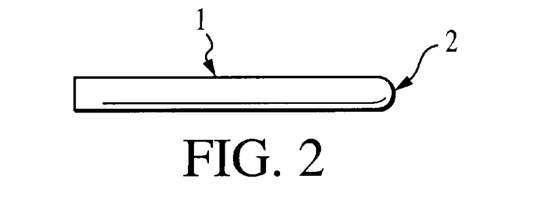
FIG. 2 shows the profile of one embodiment of the present urethral suppository.
Figure 3:
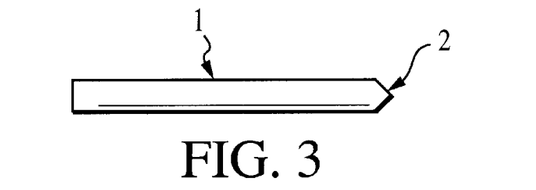
FIG. 3 shows the profile of one embodiment of the present urethral suppository.
Figure 4:
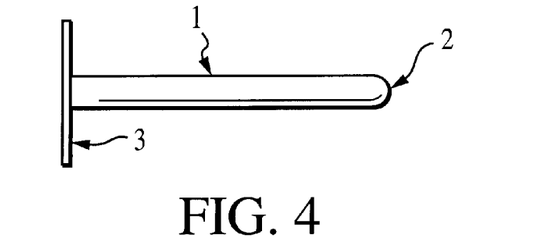
FIG. 4 shows the profile of one embodiment of the present urethral suppository.
Figure 5:
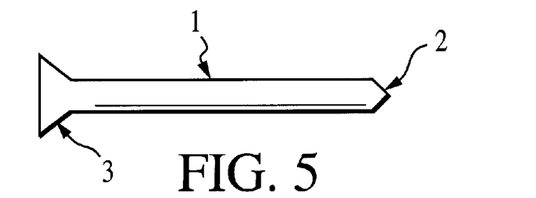
FIG. 5 shows the profile of one embodiment of the present urethral suppository.
Figure 6:
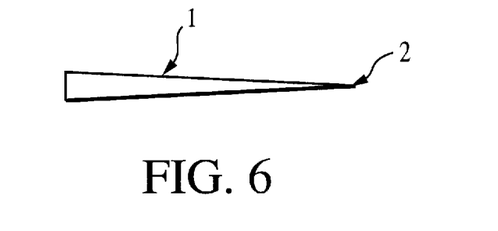
FIG. 6 shows the profile of one embodiment of the present urethral suppository.

FIGS. 2–6 show the profile or side view of some embodiments of the present suppository, while FIGS. 7–10 show the cross-sectional view of some embodiments of the present suppository. FIG. 2 shows the side view of a suppository with a straight shaft 1 and a rounded tip 2. FIG. 3 shows the side view of a suppository with a straight shaft 1 and a pointed tip 2. FIG. 4 shows the side view of a suppository with a straight shaft 1, a rounded tip 2, and flat base or stop 3 attached to the end of the shaft 1 distal to the tip 2. FIG. 5 shows the side view of a suppository with a straight shaft 1, a pointed tip 2, and flared base or stop 3 attached to the end of the shaft 1 distal to the tip 2. FIG. 6 shows the side view of a suppository which is tapered along the entire length of the shaft 1 and has a pointed tip 2.

Figure 7:
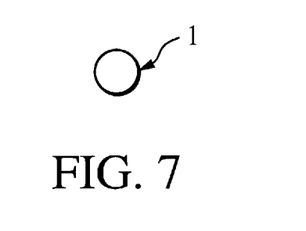
FIG. 7 shows a cross-sectional view of one embodiment of the present urethral suppository.
Figure 8:
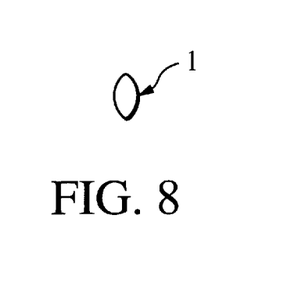
FIG. 8 shows a cross-sectional view of one embodiment of the present urethral suppository.
Figure 9:
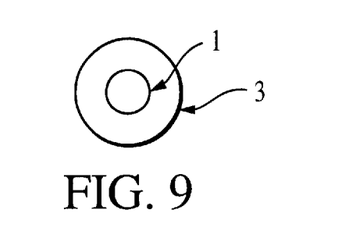
FIG. 9 shows a cross-sectional view of one embodiment of the present urethral suppository.
Figure 10:
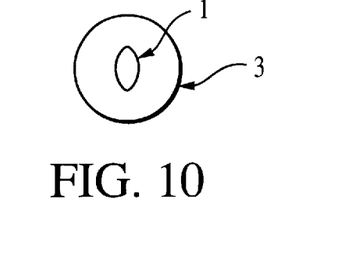
FIG. 10 shows a cross-sectional view of one embodiment of the present urethral suppository.

The present suppository is not limited to any particular cross-sectional shape. As shown in FIGS. 7–10, the present suppositories may be either circular, elliptical, oblong, or football-shaped in cross-section. Circular and elliptical cross-sectional shapes are preferred. FIG. 7 shows the cross-sectional view of a suppository which does not have a base or stop 3 and in which the shaft 1 is substantially circular in cross-section. FIG. 8 shows the cross-sectional view of a suppository which does not have a base or stop 3 and in which the shaft 1 is substantially oblong in cross-section. FIG. 9 shows the cross-sectional view of a suppository which has a base or stop 3 which is substantially circular and in which the shaft 1 is substantially circular in cross-section. FIG. 10 shows the cross-sectional view of a suppository which has a base or stop 3 which is substantially circular and in which the shaft 1 is substantially oblong in cross-section.

In one preferred embodiment, the suppository has a round or pointed tip to facilitate entry into the urethra (see FIGS. 2–5). Alternatively, the suppository may be tapered along all of or at least a substantial part of its length (see FIG. 6). The base of the suppository may be distended or flared to provide a built-in stop, so that the depth of the insertion may be determined by the length from the tip of the suppository to the beginning of the flare (see FIGS. 4 and 5). Alternatively, the base of the suppository may be attached to a piece of foil, plastic, or paper or attached to the inside of the tip of a condom in order to set the depth of insertion.

The present suppositories will typically have a cross-section having a maximum dimension of from about 0.1 mm to about 25 mm, preferably from about 1 mm to about 10 mm, particularly from about 2 mm to about 6 mm, along the portion of the suppository intended to be inserted into the urethra. Although there is in principal no lower limit on the minimum cross-sectional dimension along the portion of the suppository intended to be inserted into the urethra, practically speaking, the suppository should be thick enough to retain sufficient structural integrity to permit insertion of the suppository into the urethra without breaking or significantly bending the suppository.

As noted above, the present suppository may have a shape in which the base of the suppository is distended or flared. The distended or flared portion of the suppository will typically have a minimum dimension of at least about 5 mm, preferably at least about 10 mm. Although there is in principal no upper limit on the maximum cross-sectional dimension of the distended or flared portion of the suppository, practically speaking, it is not necessary to make the distended or flared portion any larger than what is required to prevent insertion of the suppository into the urethra beyond the point at which the distended or flared portion begins.

Typically, the suppository will contain sufficient amounts of (a) and (b) such that administration of a single suppository is sufficient to provide the desired result. Thus, a suppository would typically contain: (a) 0.1 $\mu$g to 10 mg, preferably 10 $\mu$g to 1000 $\mu$g (for transurethral administration), preferably 25 $\mu$g to 2500 $\mu$g (for meatal administration), of prostaglandin $E_1$, or 0.1 $\mu$g to 10 $\mu$g, preferably 10 $\mu$g to 1000 $\mu$g (for transurethral administration), preferably 25 $\mu$g to 2500 $\mu$g (for meatal administration), of prostaglandin $E_2$; and (b) 25 to 100 pig penile units, preferably 50 to 100 pig penile units, of the 15-hydroxyprostaglandindehydrogenase inhibitor.

In a particularly preferred embodiment, the present suppository contains 0.02 to 2 mg of oleic acid per each mg of prostaglandin $E_2$ (i.e., a 0.02:1 to 2:1 weight ratio of oleic acid:prostaglandin $E_2$). In another particularly preferred embodiment, the present suppository contains prostaglandin $E_2$ and palmitic acid in a prostaglandin $E_2$:palmitic acid weight ratio of 0.09:1 to 9:1.

In a preferred embodiment, the present suppositories are characterized as having a pH of 3 to 7, preferably 4 to 6. Such suppositories may be prepared by simply adding a sufficient amount of a pharmaceutically acceptable acid or base, e.g., HCl or NaOH to adjust the pH to the desired value. In a particularly preferred embodiment, one may add to each unit dose the residual powder from 0.5 ml of a 0.01 Molar aqueous solution of a pharmaceutically acceptable citrate salt, e.g., sodium citrate, which has the desired pH. For example, 0.5 ml of 0.01 Molar sodium citrate at pH 4.5 is lyophilized, and the powdered residue is added to a unit dose of prostaglandin $E_2$ in polyethylene glycol (PEG) MW 1450. Upon insertion of this dose into the urethra, the lyophilized citrate will dissolve and buffer the pH of the urethra to about pH 4.5 and thereby enhance the activity of the prostaglandin $E_2$ as the PEG pellet dissolves.

In a second embodiment, the present invention provides a method for treating male erectile dysfunction, by administering the present suppository to a patient in need thereof. The present method may be carried out by either transurethral administration or meatal administration of the present suppository.

Figure 1:
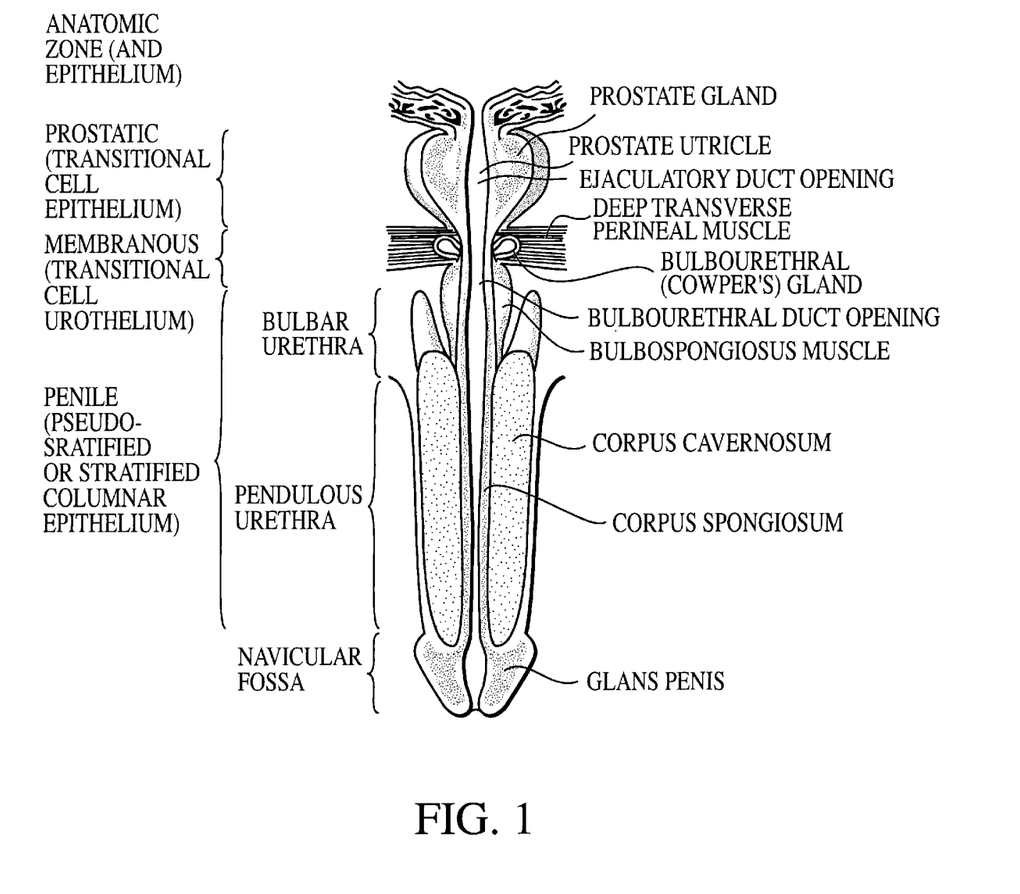
FIG. 1 is a cross-sectional view of the male urethra.

As shown in FIG. 1, the male penile urethra consists of three segments: the bulbar urethra, the pendulous urethra, and the navicular fossa. The term "transurethral administration" as used herein refers to the administration of agents to the bulbar and pendulous urethra which are covered by pseudostratified or stratified columnar epithelium. The term "meatal administration" as used herein refers to the administration of agents to the urethra of the navicular fossa and/or to the penile meatus (as shown in FIG. 1) that are covered by stratified squamous epithelium. Meatal administration is thus essentially the same as topical administration with respect to the difficulty of administering an effective transdermal dose. Conventionally, a meatal dose of a vasoactive prostaglandin would typically be expected to be 10 to 20 (or more) times greater than a transurethral dose due to the difficulty of traversing the denser epithelium. However, the present suppositories exhibit the improvement of making meatal administration feasible and effective even when using the same dosage as effective in transurethral administration.

Meatal administration is preferred over transurethral administration for a number of reasons. Meatal administration is generally easier to carry out than transurethral administration and may be the only possible means of administration in patients with narrowing or scarring of the urethra. The depth of insertion of the suppository in meatal administration is, as measured from the external opening of the penis, between 2 mm and 60 mm. In contrast, the depth of insertion of the suppository in transurthral administration is, as measured from the external opening of the penis, greater than 50 mm. Meatal or transurethral administration may be easily effected by selection of a suppository with a shaft of the appropriate length and a distended or flared base and insertion of the suppositories to the depth of the distended or flared base.

Typically, the suppository is inserted into the urethra 1 to 50 minutes, preferably 10 to 20 minutes, prior to the time of commencing sexual intercourse. Meatal administration may result in a slower onset of the effect of the active agent and, thus, may preferably be carried out earlier than transurethral administration.

Those suppositories in which component (c) dissolves or melts in the urethra are simply inserted into the urethra. Those suppositories in which component (c) releases components (a) and (b) in the urethra but does not itself dissolve or melt in the urethra are preferably inserted into the urethra to a depth which leaves a portion of the suppository protruding from the urethra, left in the urethra until the desired affect is achieved, and then removed from the urethra by means of the protruding portion.

Of course, it is also to be understood that the prostaglandin $E_1$ or prostaglandin $E_2$ need not be administered simultaneously with the 15-hydroxyprostaglandindehydrogenase inhibitor. Rather, the 15-hydroxyprostaglandindehydrogenase inhibitor may be preadministered in a first suppository followed by treatment with the prostaglandin in a second suppository. Pretreatment or simultaneous treatment with a 15-hydroxyprostaglandindehydrogenase inhibitor decreases the burning sensation associated with the administration of the prostaglandin. In addition, the blocking of the PGDH enhances tremendously the absorption and effectiveness of the prostaglandin leading to a remarkably lower dose requirement.

Since PGDH degrades most pharmacologically active prostaglandins, not just $PGE_1$ and $PGE_2$, the inhibition of PGDH may be used in combination with any prostaglandin or prostaglandin analogue which is suitable for inclusion in the present compositions by nature of its vasodilating activity.

The present suppositories may be manufactured by any standard method known to the art, including but not limited to extrusion, casting, and injection molding. For example, the present suppositories may be prepared by forming, under sterile conditions, an intimate mixture containing the appropriate relative amounts of components (a), (b), and (c) at a temperature above the melting point of component (c) and then forming the suppository of the desired shape by extrusion, casting, or injection molding.

The present suppositories and methods offer a number of advantages as compared with conventional compositions and methods for treating male erectile dysfunction. In particular, the present suppositories and methods:

1. Eliminate the need for a device to administer the active agent;
2. Allows the use of a prostaglandin dosage that is remarkably smaller than the doses conventionally used with transurethral administration devices;
3. Permits manufacturing the composition with a greatly simplified process;
4. Results in a decreased exposure of the prostaglandin to light, heat, and moisture during manufacturing;
5. Results in reduced irritation to the urethra/meatus than conventional methods;
6. Allows the use of physiological concentrations of the naturally occurring prostaglandin and free fatty acids; and
7. Allows the treatment of patients with abnormal urethral anatomy; and
8. Allows the use of a meatal dose of prostaglandin that is remarkably smaller than previously demonstrated.

Other features of the invention will become apparent in the course of the following descriptions of exemplary embodiments which are given for illustration of the invention and are not intended to be limiting thereof.

EXAMPLES

1. PGDH Activity

A. Pig Penile Urethral Mucosa Preparation:

Fresh hog penises from sexually mature animals are obtained from a local slaughter house. They are immediately washed in tap water and then in normal saline. The urethra corresponding to the section extending from the fossa navicularis and extending to the membraneous region of the urethra is separated from the corpus spongiosum. This region is called the penile urethra, and the corresponding length of the urethra is measured in millimeters and recorded. The weight of the urethra is also recorded. The mucosa is homogenized with four volumes of an ice-cold 100 mM potassium phosphate buffer (pH 7.5) containing 1 mM EDTA. Following centrifugation at 15,000 g for 15 minutes, the resultant supernatant fraction is used as the enzyme source of the penile mucosa.

B. 15-Hydroxyprostaglandindehydrogenase (PGDH) Activity Determination:

Spectrophotometric Analysis:

As a substrate, prostaglandin $E_1$ is incubated with the pig penile urethral mucosa prepared above. The reaction mixture is contained in a total volume of 2.0 ml of the same buffer used above for the preparation of the pig penile urethral mucosa preparation.

Prostaglandin $E_1$ (50 microM) and NAD (300 microM) are used as substrates. The reaction is initiated by the addition of the prostaglandin $E_1$. Incubation is done at 37° C. and is terminated by the addition of 0.5 mL of 2NaOH. The oxidation of the prostaglandin is assayed by monitoring the reduction of NAD+ at 340 nanometers in a spectrophotometer. Reaction times are adjusted so that the initial quantity of prostaglandin is oxidized by 50 to 80%.

Radiochemical determination: The same reactions conditions listed for spectrophotometric analysis are used except that (5, 6, 8, 11, 12, 14, 15(n)-$^3$H)-prostaglandin $E_2$ (specific activity, 171 Ci, mmol) from Dupont de Nemours is used as a typical substrate. Any other tritiated prostaglandin substrate can be utilized in this assay. To terminate the reaction, methanol precipitation (75% volume/volume)) is performed. then, water is added to dilute the methanol to 10 volume percent. Soluble phase extractions are performed using octadecyl 18-C silica cartridges (J. T. Baker. Deventer, Holland. Dried extracts are run on 20×20, 60A silica plates using the organic phase of ethyl acetate/acetic acid/isooctane/water (11:2:5:10:). Authentic prostaglandin $E_2$. 15-keto-prostaglandin $E_2$, and 13, 14-dihydro-15-keto-prostaglandin $E_2$ are comigrated on separate lanes. After localization of the compounds using phosphomolybdic spray, the silica is scraped, and the respective amounts of prostaglandin in $E_2$ and 15-keto-prostaglandin $E_2$ are determined by radioactive counting. A mU is defined as that amount of enzyme which oxidizes 1 n mole of prostaglandin $E_2$ or $E_1$ per min at 37° C. pH 7.4. The number of mU PGDH per mm of pig penile urethra is then calculated by dividing the total number of mU by the mm of urethra used to prepare the enzyme.

II. PGDH Inhibitor Activity Determination

In the context of the present invention, one pig penile unit of PGDH inhibition activity is defined as the quantity of inhibitor that prevents one percent of the quantity of prostaglandin present from being oxidized using the assay described below.

Spectrophotometric: Using the above listed spectrophotometric analytical system for PGDH activity, the inhibitor in question is added to the reaction mixture prior to the addition of the prostaglandin $E_1$. At termination of the reaction, the quantity of the prostaglandin $E_1$ degraded is calculated and compared to the reaction without the inhibitor. Percent inhibition is defined as B/A×100 where A=nmoles of prostaglandin oxidized without inhibitor.
B=nmoles prostaglandin oxidized with inhibitor.

For example, if A=50 nmoles and B=25 nmoles with inhibitor C, then inhibitor C gives 25/50×100 or 50% inhibition in this assay.

Radiochemical Determination: The assay for inhibition is run with and without inhibitor added as listed above in the determination of PGDH activity radiochemically. A given inhibitor is added to the reaction mixture just prior to the addition of the prostaglandin $E_2$ being analyzed and the analysis performed as listed. The quantity of prostaglandin oxidized is calculated and interpreted as listed above for spectrophotometric analysis of inhibitor activity.

Reference Example

An aqueous solution containing 250 µg of PGE2, and 150 µg of phentolamine hydrochloride was applied directly to the urethra of a 42 year old male with a history of erectile dysfunction. An erection was produced in 10 minutes. It lasted for 60 minutes.

Example 1

1.500 Grams of ethyl stearate, 6.25 mg of PGE 2, and 62.5 mg of oleic acid were placed in a Pyrex test tube and heated to about 100° F. on a hot plate with periodic agitation. The mixture rapidly melted to afford a clear solution. A standard laboratory micropipette (Justor 1100 BG manufactured by Nichiryo and available from Sigma, St. Louis. Mo. USA with volume dispensed adjustable from 10.0 to 100.0 microliters; and Sigma pipette tips—catalog #B-6429) was repeatedly dipped into this solution and aspirated with the volume set at 37 microliters. The solution rapidly solidified at ambient room temperature (71° F.) and the resultant suppository was removed by pressing a paper clip into the tip of the pipette. Approximately 100 suppositories were made in a two hour period using this method. Subsequent weighing showed that 96% of the suppositories weighed 31±0.5 mgs. Similar results were obtained when palmitic acid was substituted for oleic acid.

Example 2

Five men without any history of erectile dysfunction inserted a suppository composed of 125 µg of PGE 2, 1.25 mg of oleic acid in 30 mg of ethyl stearate, which measured 18 mm in length and about 2 nm in maximum diameter, prepared as described in Example 1, into their urethral meatus. The change in cavernosal arterial peak systolic blood flow was monitored before and after insertion with a Knoll/Midas® doppler ultrasound device. All five subjects experienced erectile responses that were sufficient for penetration. This length suppository delivers a meatal dose.

Example 3

A 46-year-old white male with multiple etiologies of erectile dysfunction including atherosclerosis, tobacco use, antidepressant use, and a 30-year history of phimosis and resulting obliteration of the glans penis by scarring was evaluated. Due to urethral strictures (from scar tissue), the urethra was narrowed to about 2 mm near the tip of the penis making insertion of a catheter impossible. A suppository (as described in Example 1) was easily and painlessly inserted into the urethra occluding it at the stricture. After 20 minutes, the patient experienced a firm erection, which lasted 60 minutes.

Example 4

Five men all with a history with erectile dysfunction inserted the same suppository described in Example 1 into their respective urethras. All five patients experienced erectile responses sufficient for penetration over the next 30 minutes.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A pharmaceutical composition, comprising:

(a) a prostaglandin vasodilator;

(b) 15-hydroxyprostaglandin dehydrogenase inhibitor (15-PGDH); and (c) a base material that is solid at room temperature and releases components (a) and (b) when inserted in the urethra;

wherein components (a) and (b) are present in synergistically effective amounts.

2. The pharmaceutical composition of claim 1, wherein component (c) melts or dissolves when inserted in the urethra to release components (a) and (b).

3. The pharmaceutical composition of claim 1, wherein component (c) does not melt or dissolve when inserted in the urethra to release components (a) and (b).

4. The pharmaceutical composition of claim 1, wherein said prostaglandin vasodilator is selected from the group consisting of prostaglandin E-1; prostaglandin E-2; prostaglandin F-2α; prostaglandin A-1; prostaglandin B-1; prostaglandin D-2; prostaglandin E-M; prostaglandin F-M; prostaglandin H-2; prostaglandin I-2; 19-hydroxy-prostaglandin A-1; 19-hydroxy-prostaglandin B-1; prostaglandin A-2; prostaglandin B-2; 19-hydroxy-prostaglandin A-2; 19-hydroxy-prostaglandin B-2; prostaglandin B-3; prostaglandin F-1α; 15-methyl-prostaglandin F-2α; 16,16-dimethyl-$\Delta^2$-prostaglandin E-1 methyl ester; 15-deoxy-16-hydroxy-16-methyl-prostaglandin E-1 methyl ester; 16,16-dimethyl-prostaglandin E-2; 11-deoxy-15-methyl-prostaglandin E-1; 16-methyl-18,18,19,19-tetrahydrocarbacyclin; (16RS)-15-deoxy-16-hydroxy-16-methyl-prostaglandin E-1 methyl ester; (+)-4,5-didehydro-16-phenoxy-α-tetranor-prostaglandin E-2 methyl ester; 11-deoxy-11a,16,16-trimethyl-prostaglandin E-2; (+)-11a,16a,b-dihydroxy-1,9-dioxo-1-(hydroxymethyl)-16-methyl-trans-prostene; 9-chloro-16,16-dimethyl-prostaglandin E-2; arboprostil; iloprost; and CL 115,347.

5. The pharmaceutical composition of claim 1, wherein said prostaglandin vasodilator is selected from the group consisting of prostaglandin E-1, prostaglandin E-2, prostaglandin F-2α, prostaglandin D-2, prostaglandin F-1α, and 15-methyl-prostaglandin F-2α.

6. The pharmaceutical composition of claim 1, wherein said prostaglandin vasodilator is prostaglandin $E_1$.

7. The pharmaceutical composition of claim 1, wherein said prostaglandin vasodilator is prostaglandin $E_2$.

8. The pharmaceutical composition of claim 1, wherein said 15-hydroxyprostaglandindehydrogenase inhibitor is selected from the group consisting of glycyrrhizic acid, licorice, DHEA, spironolactone, sofalcone, etodolac, indomethacin, sulindac, sulphasalazine, anologs of sulphasalazine, capric acid, lauric acid, myristic acid, palmitic acid, stearic acid, arachidic acid, oleic acid, linoleic acid, and arachadonic acid.

9. The pharmaceutical composition of claim 6, which comprises 0.1 μg to 10 mg of said prostaglandin $E_1$; and 25 to 100 units of said 15-hydroxyprostaglandindehydrogenase inhibitor.

10. The pharmaceutical composition of claim 6, which comprises 0.1 μg to 10 mg of said prostaglandin $E_1$; and 0.1 μg to 20 mg of a 15-hydroxyprostaglandindehydrogenase inhibitor selected from the group consisting of capric acid, lauric acid, myristic acid, palmitic acid, stearic acid, arachidic acid, oleic acid, linoleic acid, and arachadonic acid.

11. The pharmaceutical composition of claim 6, which comprises 0.1 μg to 10 mg of said prostaglandin $E_1$; and 0.1 mg to 20 mg of a 15-hydroxyprostaglandindehydrogenase inhibitor selected from the group consisting of etodolac, indomethacin, and sulindac.

12. The pharmaceutical composition of claim 7, which comprises 0.1 μg to 10 mg of said prostaglandin $E_2$; and 25 to 100 units of said 15-hydroxyprostaglandindehydrogenase inhibitor.

13. The pharmaceutical composition of claim 7, which comprises 0.1 μg to 10 mg of said prostaglandin $E_2$; and 0.1 μg to 20 mg of a 15-hydroxyprostaglandindehydrogenase inhibitor selected from the group consisting of capric acid, lauric acid, myristic acid, palmitic acid, stearic acid, arachidic acid, oleic acid, linoleic acid, and arachadonic acid.

14. The pharmaceutical composition of claim 7, which comprises 0.1 μg to 10 mg of said prostaglandin $E_2$; and 0.1 mg to 20 mg of a 15-hydroxyprostaglandindehydrogenase inhibitor selected from the group consisting of etodolac, indomethacin, and sulindac.

15. The pharmaceutical composition of claim 7, wherein the 15-PGDH is an aliphatic or aromatic carboxylic acid.

16. The pharmaceutical composition of claim 15, wherein the 15-PGDH is selected from a $C_8$–$C_{31}$ straight chain, branched, saturated, mono-unsaturated, or poly-unsaturated aliphatic carboxylic acid.

17. The pharmaceutical composition of claim 16, wherein the 15-PGDH is a fatty acid.

18. The pharmaceutical composition of claim 17, wherein the fatty acid is selected from arachidic acid, arachadonic acid, capric acid, lauric acid, linoleic acid, myristic acid, oleic acid, palmitic acid, and stearic acid.

19. The pharmaceutical composition of claim 18, wherein the fatty acid is selected from linoleic acid, oleic acid, and palmitic acid.

20. The pharmaceutical composition of claim 19, wherein the fatty acid is palmitic acid.

21. The pharmaceutical composition of claim 19, wherein the fatty acid is oleic acid.

22. The pharmaceutical composition of claim 12, wherein the 15-PGDH is an aliphatic or aromatic carboxylic acid.

23. The pharmaceutical composition of claim 22, wherein the 15-PGDH is selected from a $C_8$–$C_{31}$ straight chain, branched, saturated, mono-unsaturated, or poly-unsaturated aliphatic carboxylic acid.

24. The pharmaceutical composition of claim 23, wherein the fatty acid is selected from linoleic acid, oleic acid, and palmitic acid.

25. The pharmaceutical composition of claim 24, wherein the fatty acid is palmitic acid.

26. The pharmaceutical composition of claim 24, wherein the fatty acid is oleic acid.

* * * * *

UNITED STATES PATENT AND TRADEMARK OFFICE
CERTIFICATE OF CORRECTION

PATENT NO.     : 6,414,027 B1
DATED          : July 2, 2002
INVENTOR(S)    : Gary W. Neal It is certified that error appears in the above-identified patent and that said Letters Patent is hereby corrected as shown below:

Column 2,
Line 38, "topical, mental," should read -- topical, meatal --;

Column 11,
Line 35, "Mg" should read -- mg --.

Column 19,
Line 49, "anologs" should read -- analogs --.

Signed and Sealed this

Third Day of December, 2002

JAMES E. ROGAN
*Director of the United States Patent and Trademark Office*